United States Patent
Begg (10) Patent No.: US 9,039,723 B2
(45) Date of Patent: *May 26, 2015

(54) SURGICAL PUNCTURE ACCESS (71) Applicant: Massachusetts Institute of Technology, Cambridge, MA (US)

(72) Inventor: Nikolai David Michael Begg, Boston, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 218 days.

This patent is subject to a terminal disclaimer.

(21) Appl. No.: 13/849,942

(22) Filed: Mar. 25, 2013

(65) Prior Publication Data
US 2013/0274776 A1    Oct. 17, 2013

Related U.S. Application Data (63) Continuation of application No. 13/204,356, filed on Aug. 5, 2011, now Pat. No. 8,419,764.

(51) Int. Cl.
*A61B 17/34* (2006.01)
*A61B 17/3211* (2006.01)

(52) U.S. Cl.
CPC ......... *A61B 17/3494* (2013.01); *A61B 17/3496* (2013.01); *A61B 2017/32113* (2013.01); *A61B 2017/3454* (2013.01)

(58) Field of Classification Search
CPC ............ A61B 5/1411; A61B 17/3496; A61B 5/150022; A61B 5/15142; A61B 2017/32113; A61B 5/15113; A61B 5/15117; A61B 5/15144; A61B 5/15194; A61M 5/3275; A61M 2005/3267; A61M 5/326

USPC ................................. 606/167, 181–183, 185
See application file for complete search history.

(56) References Cited

U.S. PATENT DOCUMENTS 4,535,773 A    8/1985   Yoon
5,053,010 A    10/1991  McGary et al.
5,211,629 A    5/1993   Pressly et al.
(Continued)

FOREIGN PATENT DOCUMENTS

WO    WO 2013/022604    2/2013

OTHER PUBLICATIONS

"International Application Serial No. PCT/US2012/048221, Preliminary Report on Patenability mailed Feb. 20, 2014", 7 pages.
(Continued)

*Primary Examiner* — Katherine M Shi
(74) *Attorney, Agent, or Firm* — Strategic Patents, P.C.

(57) ABSTRACT

A surgical device mitigates over-puncture with a bias spring that biases a leading, cutting edge in the opposite direction of the anticipated over-puncture. An associated locking mechanism is configured to release the force of the bias spring in a direction counter to the direction of insertion when the tension force of tissue against the cutting edge is released. Thus, when an opening in the tissue forms, the tension is released and the cutting edge can move opposite to the direction of insertion of the surgical device at the same time that an applied force drives the instrument in the direction of insertion. In this manner, the spring and locking mechanism cooperate to move the cutting edge opposite to the direction of insertion as soon as an incision is made.

12 Claims, 8 Drawing Sheets

(56) References Cited

U.S. PATENT DOCUMENTS

| | | |
|---|---|---|
| 5,320,610 A | 6/1994 | Yoon |
| 5,336,176 A | 8/1994 | Yoon |
| 5,514,111 A | 5/1996 | Phelps |
| 5,632,733 A | 5/1997 | Shaw |
| 6,090,077 A | 7/2000 | Shaw |
| 7,351,224 B1 | 4/2008 | Shaw |
| 7,927,303 B2 | 4/2011 | Wyrick |
| 2006/0173480 A1 | 8/2006 | Zhang |
| 2007/0185515 A1 | 8/2007 | Stout |
| 2011/0130744 A1 | 6/2011 | Kassab et al. |
| 2013/0035709 A1 | 2/2013 | Begg |

OTHER PUBLICATIONS

Loschak, Paul et al., "Cranial Drilling Tool with Retracting Drill Bit Upon Skull Penetration", Biorobotics.harvard.edu/pubs/2012.contrib/DMD2012_Loschak Aug. 4, 2012, 1 page.

"International Application Serial No. PCT/US2012/048221, Search Report and Written Opinion mailed Oct. 16, 2012", 6 pages.

"U.S. Appl. No. 13/204,356, Notice of Allowance mailed Feb. 5, 2013", 20 pages.

Fig. 9

SURGICAL PUNCTURE ACCESS

CROSS-REFERENCE TO RELATED APPLICATIONS

This application is a continuation of U.S. patent application Ser. No. 13/204,356 filed on Aug. 5, 2011, which is hereby incorporated by reference in its entirety.

BACKGROUND

In minimally invasive surgical procedures, one or more tissue layers must sometimes be punctured without direct visualization of an instrument tip in order to gain access to a body cavity, duct, or the like. The instruments for such procedures are generally long and slender with high axial stiffness. In use, a surgeon or other user applies sufficient axial force so that the instrument can penetrate into the tissue by cutting, tearing or separating tissue fibers.

At the point of puncture, or the instant when the tissue opens at the tip of the instrument, the force applied to the instrument by tissue tension goes to zero while the force applied by the user remains as a net force accelerating the instrument into the surgical site. Device designers have attempted to improve instruments to mitigate this forward driving force and subsequent acceleration by offering dynamic blade covers, blunt-tipped devices, and other features that indirectly address the problem of over-puncture by seeking to reduce the harmful effects when an over-puncture occurs.

There remains a need for puncture devices that reduce or eliminate the over-puncture event, rather than addressing consequences of an over-puncture after it occurs.

SUMMARY

A surgical device mitigates over-puncture with a bias spring that biases a leading, cutting edge in the opposite direction of the anticipated over-puncture. An associated locking mechanism is configured to release the force of the bias spring in a direction counter to the direction of insertion when the tension force of tissue against the cutting edge is released. Thus, when an opening in the tissue forms, the tension is released and the cutting edge can move opposite to the direction of insertion of the surgical device at the same time that an applied force drives the instrument in the direction of insertion. In this manner, the spring and locking mechanism cooperate to move the cutting edge opposite to the direction of insertion as soon as an incision is made.

DRAWINGS

The invention may be more fully understood with reference to the accompanying drawings wherein.

DETAILED DESCRIPTION

Disclosed herein are systems and methods for surgical puncture access, and in particular, puncture access using a retraction mechanism that retracts a blade in a direction opposite to a puncture force when a puncture is achieved and the resistive force of intervening tissue is removed. Although the disclosed retraction mechanisms are intended for a trocar in a surgical procedure, the principles of the invention have wide applicability. In a surgical context, any puncture-access device may employ similar techniques to prevent over-puncture, including a Veress needle, a venous access needle for catheter placement, an epidural or spinal tap needle, and a lung puncture device to correct a collapsed lung.

More generally, the phenomenon of over-puncture appears in areas outside medicine and the principles of the invention may be applied in numerous non-medical contexts. For example, in certain manufacturing processes, a hole is drilled through a wall or vehicle body behind which lies a pipe, electrical conduit, gas tank, or other fragile or dangerous object. A power drill may be adapted to use the principles of the invention in order to drill only through the wall and no further, retracting a drill bit or the like when a complete puncture has been achieved. In similar fashion, a drill press can be adapted to prevent a user from drilling through a part and into a drilling table or chuck. Much larger industrial drilling applications through rock or soil could similarly use these mechanisms to prevent damage due to over-drilling. All such variations that would be apparent to one of ordinary skill in the art are intended to fall within the scope of this disclosure.

Figure 1:
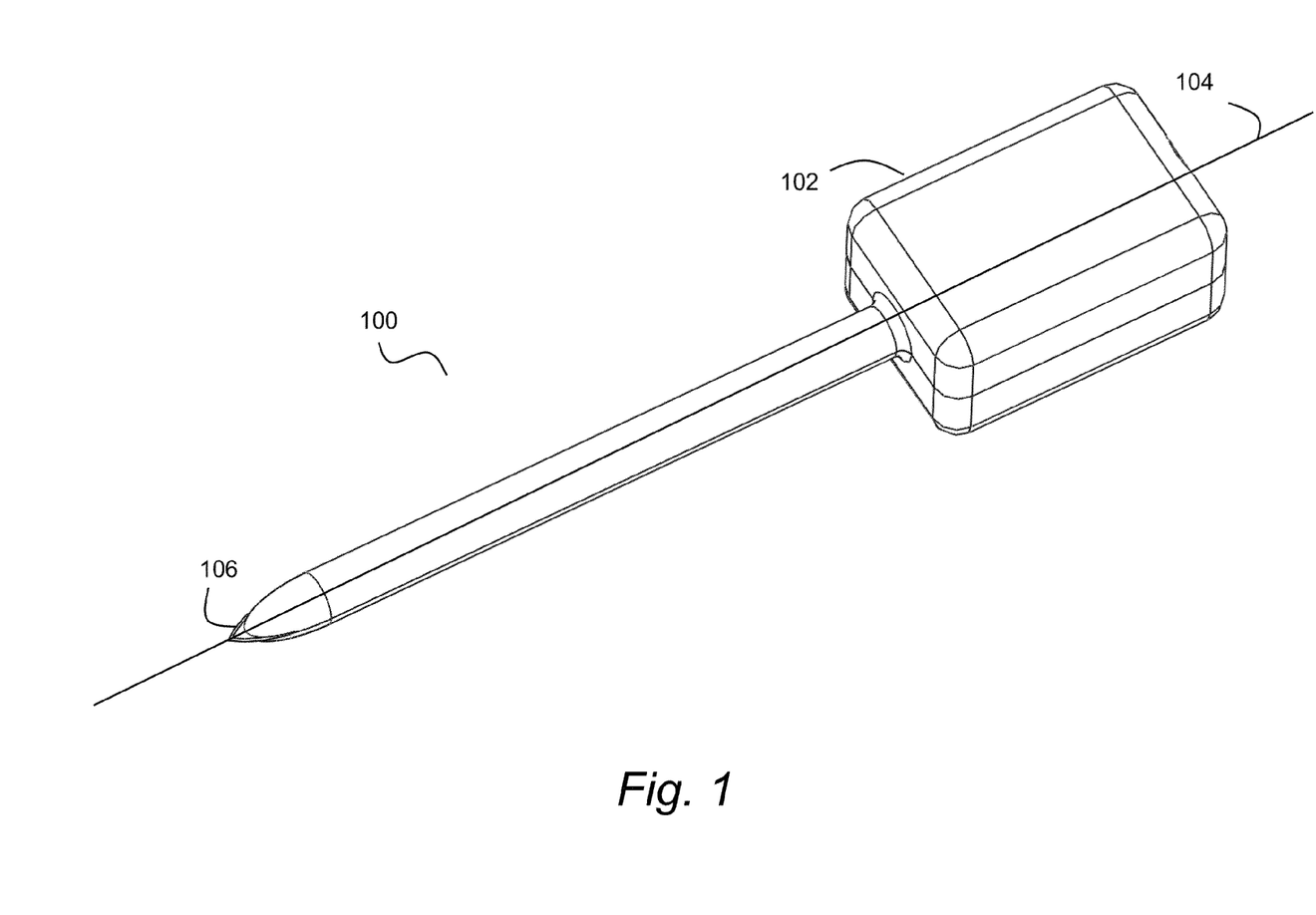
FIG. 1 is a perspective view of a device for surgical puncture access.

FIG. 1 is a perspective view of a device for surgical puncture access. In general, the device 100 may include a housing 102 with an axis 104 oriented through the housing 102 in a direction of applied force as described below. As depicted, the device 100 is in a deployed position where a functional tip 106 of an instrument such as a cutting edge of a surgical blade extends outside the housing where it can be used in a cutting procedure or the like.

Figure 2:
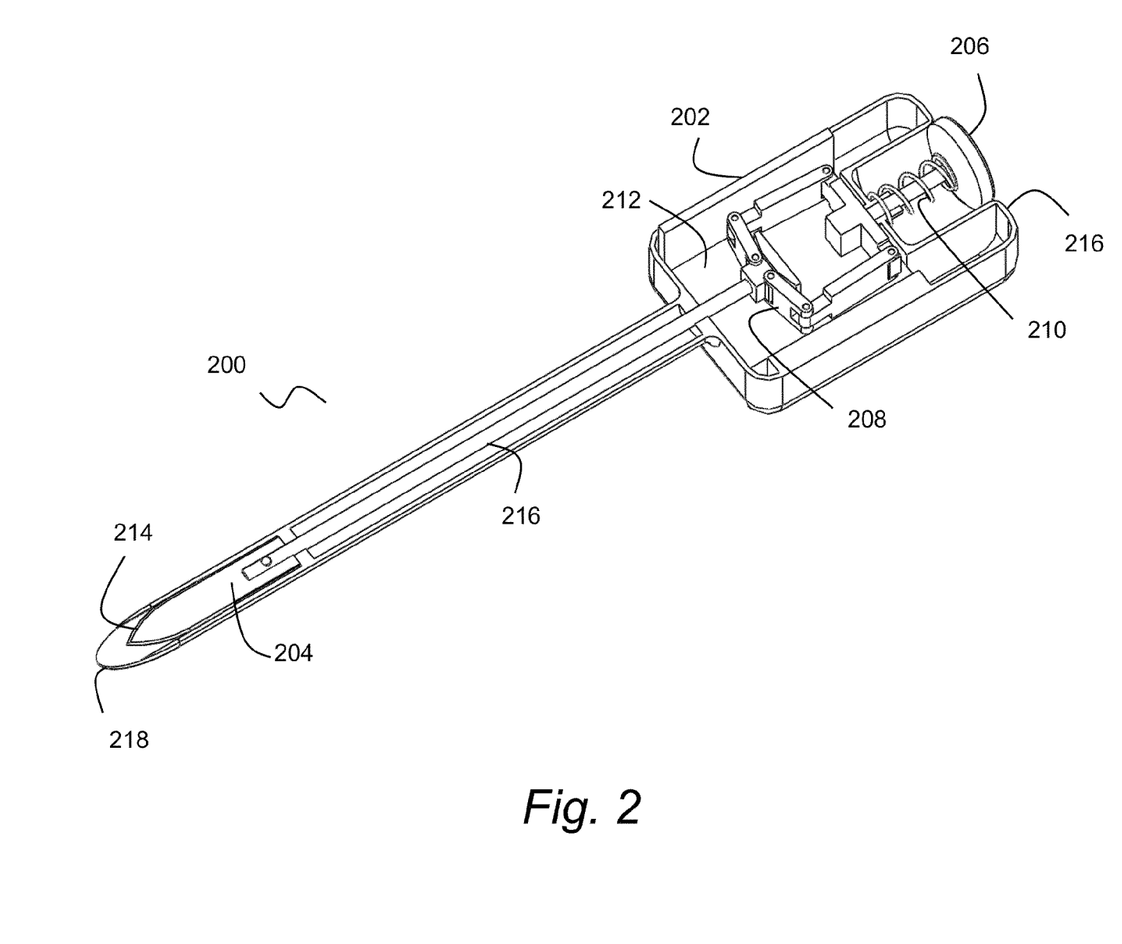
FIG. 2 is a cut-away perspective view of a device for surgical puncture access.

FIG. 2 is a cut-away perspective view of a device for surgical puncture access. In general, the device 200, which may be the device 100 described above, may include a housing 202, an instrument 204, a mechanical control 206, a locking mechanism 208, and a biasing mechanism 210.

The housing 202 may be formed of any suitable material such as biocompatible plastic or surgical stainless steel, and may enclose various components of the device 200. The housing 202 may be a trocar shaped and sized for use in a laparoscopic procedure. More generally, the housing 202 may be of any other shape and size suitable for a particular medical or industrial application as contemplated herein. The housing has an interior 212 that contains various components of the device 200.

The instrument 204 may be slidably retained within the housing so that it can move axially (i.e., along the axis 104 depicted in FIG. 1) during use. More specifically, the instrument 204 may be slidably retained within the housing 202 and movable along the axis between a first position where a functional tip of the instrument 204 extends outside the housing 202 (as depicted in FIG. 1) and a second position where the functional tip rests within the housing 202 (as depicted in FIG. 2).

The instrument 204 may include a blade 214 such as an off-the-shelf symmetrical scalpel blade or any other blade or cutting instrument, or more generally any functional tip such as a drill bit, an awl or other piercing instrument, or the like. The instrument 204 may also include a shaft 216 that mechanically couples the blade 212 to other components of the device 200. The shaft 216 may be coupled to the blade 214 with a pin, dowel, or any other permanent or removable/replaceable attachment fixture. In FIG. 2, the instrument 204 is depicted in a retracted position where the blade 204 is disposed within the housing 202. In this position, the tip of the blade 214 is shielded within an insertion end 216 of the housing that has a rounded or blunt tip so that the device 200, with the blade 214 in this retracted position does not have an exposed cutting surface. The blade 214 may be fully enclosed by a second half of the housing that is not shown here.

The mechanical control 206 may be coupled (e.g., through the locking mechanism 208) to the instrument 204 and provides a manual control to move the instrument from the second (retracted) position to the first (deployed) position. This may, for example, include a plunger as depicted or any similarly operable device such as a slide or tab on a side of the housing 202 that permits axial movement of the instrument 204 into the deployed position by a user. Thus, the mechanical control 206 may be generally operable at a first end 216 of the housing 202 distal from a second end 218 of the housing where a functional tip of the instrument 204 deploys from the housing 202.

The locking mechanism 208 may be generally configured to secure the instrument against movement toward the second (retracted) position when the instrument is in the first (deployed) position and a force is applied to the blade 214 of the instrument 204 along the axis of the housing 202 and toward the interior 212 of the housing 202, or toward the first end 216 of the housing 202 opposite the second end 216 (the insertion end). The locking mechanism 208 may also release the instrument 204 to move toward the second (retracted) position when the force applied to the blade 214 is removed.

The biasing mechanism 210 generally biases the instrument 204 toward the second position where the instrument 204, or more specifically the blade 214 or other function tip of the instrument is enclosed within the housing 202. The biasing mechanism may, for example, include a coil spring or other spring configuration coupled between the mechanical control 206 (e.g., a plunger) and the housing 202, or any other suitable spring mechanism, elastic mechanism, or the like.

The cooperation of the locking mechanism 208 and the accompanying biasing mechanism 210 is discussed below, and generally facilitates retraction of the instrument 204 in a direction opposite to the direction of puncture when the loading force on the instrument 204 decreases, e.g., after a puncture is achieved.

Figure 3:
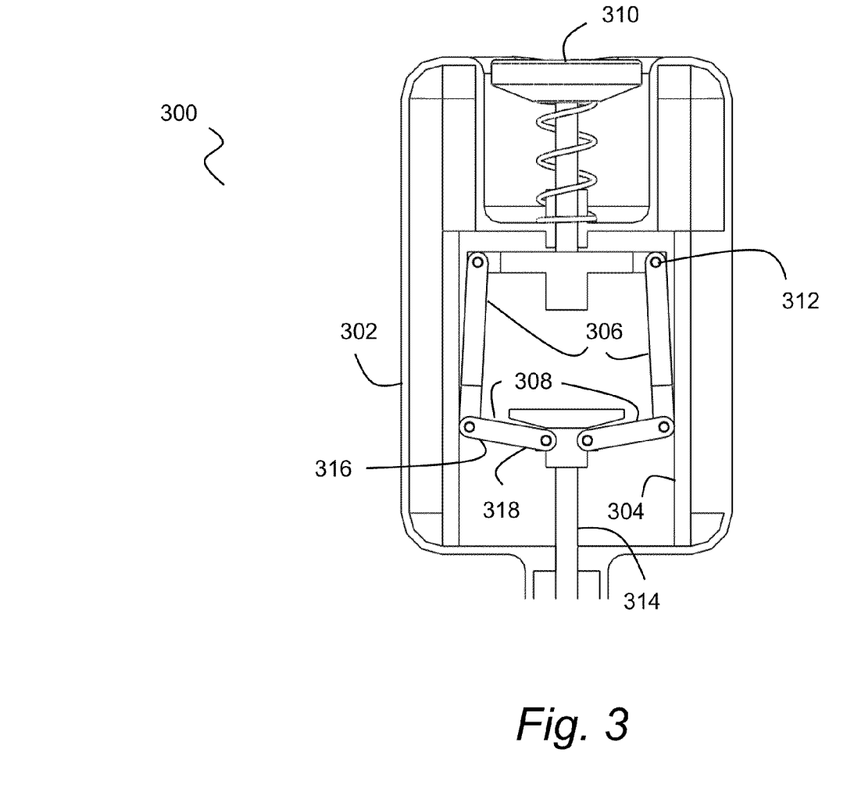
FIG. 3 is a cross-sectional view of a device for surgical puncture access.

FIG. 3 is a cross-sectional view of a device for surgical puncture access. The device 300 may include a housing 302, which may be any of the housings described above, with an interior wall 304. A locking mechanism as described above may be formed of a first plurality of members 306 and a second plurality of members 308.

The first plurality of members 306 may be coupled to a plunger 310 or other mechanical control through a base plate or the like, which may include one or more hinges 312 to permit rotation of the first plurality of members 306 during use. In general, the first plurality of members may be oriented substantially parallel to the interior wall 304 of the housing 302. In this orientation, the plunger 310 can apply a force to move an instrument connected to a shaft 314 from a retracted position inside the housing 302 to a deployed position outside the housing 302. It will be understood that being oriented substantially parallel to the interior wall 304 does not require strict mathematical parallelism. Rather, each of the first plurality of members 306 may be generally closer to parallel than normal, or otherwise oriented sufficiently close to parallel to deliver an axial force from the plunger 310 against a biasing spring or the like to move the shaft 314 forward (or downward, in FIG. 3) and deploy an instrument. By orienting the first plurality of members 306 nearly parallel to the interior wall 304, a force applied to the plunger 310 creates a relatively small normal force against the interior wall 304 and prevents the locking mechanism from locking by friction against the interior wall 304 of the housing.

The second plurality of members 306 may be hingeably coupled on a first end 316 to the first plurality of members, and coupled to the instrument (e.g., through the shaft 314) on a second end 318. The second plurality of members 306 may be oriented substantially normal to the interior wall 304 of the housing. In this orientation, the first end 316 of each of the second plurality of members 306 can apply a normal force to frictionally engage the interior wall 304 of the housing 302 in a non-sliding mechanical relationship when a load is applied to the blade or other functional tip of an instrument coupled to the shaft 314. More specifically a force applied in a direction from the deployed position to the retracted position along the axis of the housing 302 is converted through the linkages of the locking mechanism into a relatively large normal force into the interior wall 304 at the ends 316 of the second plurality of members 308.

For the second plurality of members 308, being oriented substantially normal to the interior wall 304 does not require strict mathematical orthogonality. Rather, each of the second plurality of members 308 may be generally closer to normal than parallel, or otherwise oriented sufficiently close to normal to deliver a normal force to the interior wall 304 so that the first end 316 of each of the second plurality of members 308 can frictionally engage the interior wall 304 and secure the shaft 314 against further movement toward a retracted position. This arrangement advantageously increases the locking effect of the frictional engagement as the retraction load on the shaft 314 increases.

In operation, the locking mechanism may secure an instrument against moving from a first position outside the housing 302 to a second position within the housing 302 by frictionally engaging the interior wall 304 of the housing 302 with a force proportional to a load applied to the functional tip in a direction from the first position to the second position along the axis of the housing 302. When the load is removed, the complementary normal forces against the interior wall 304 are similarly removed, and the spring or other biasing mechanism can return the instrument to the second (retracted) position.

It will be understood that while two pairs of members are shown, any number of members may be used. For example, the locking mechanism may use three or more pairs of members in a radial configuration within a cylindrical housing interior. Similarly, the principles of the locking mechanism may be usefully adapted to employ a single first and second member in an asymmetrical configuration. Thus, the arrangement of components in the locking mechanism of FIG. 3 is provided by way of example only, and is not intended to limit the scope of the invention.

Figure 4:
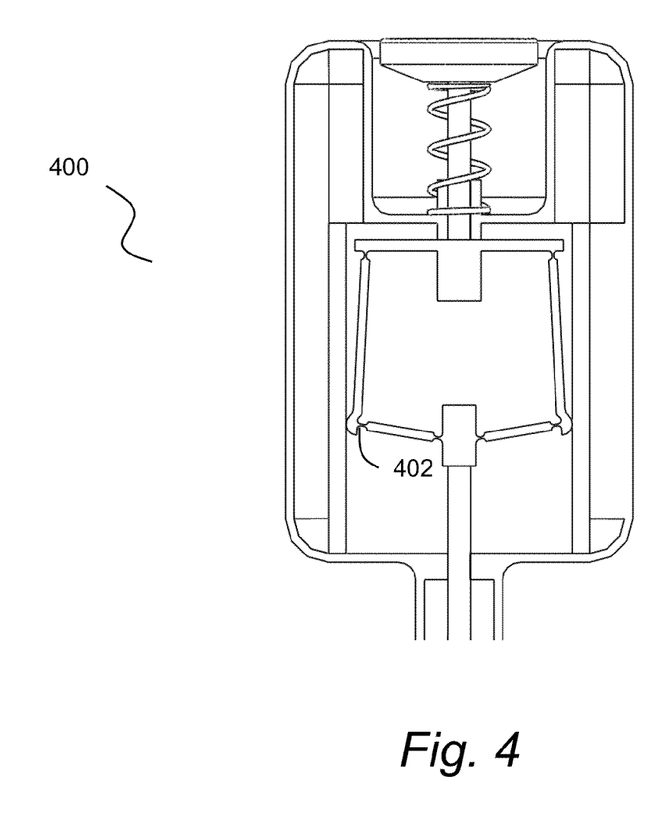
FIG. 4 is a cross-sectional view of a device for surgical puncture access.

FIG. 4 is a cross-sectional view of a device for surgical puncture access. In an alternative configuration of the device 400, the first and second plurality of members may be formed of a monolithic piece of material with flexural hinges 402 such as corner-filleted hinging elements in place of the pin-based hinge elements depicted in FIG. 3. Operation of this device 400 is otherwise similar to the device 300 depicted in FIG. 3.

Figure 5:
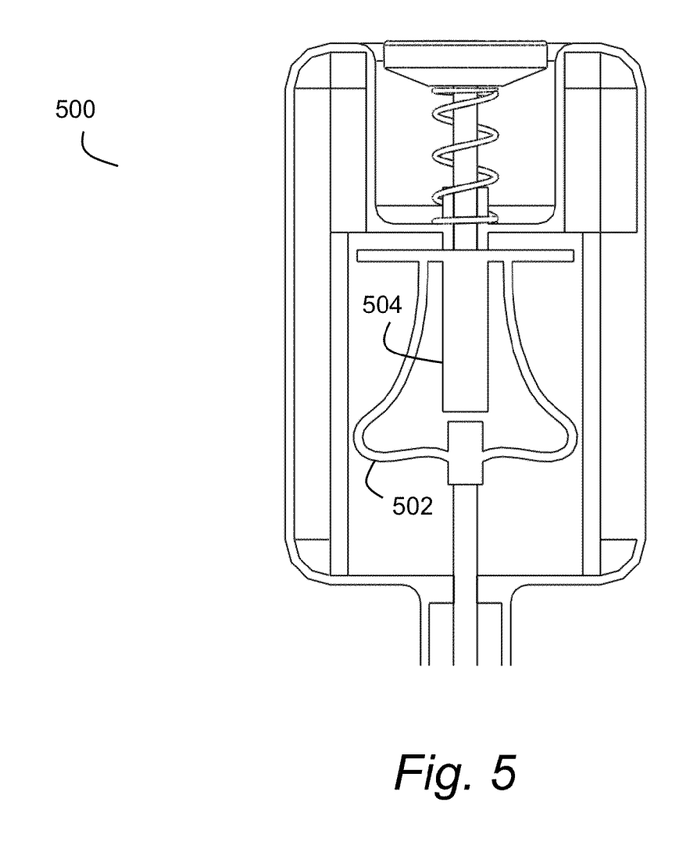
FIG. 5 is a cross-sectional view of a device for surgical puncture access.

FIG. 5 is a cross-sectional view of a device for surgical puncture access. In an alternative configuration of the device 500, the locking mechanism may be formed of curved elements 502 that generally reproduce the loading schemes discussed above without use of hinges or discrete structural members.

The device 500 may include a mechanical stop 504 positioned to prevent collapse of the locking mechanism and comprise of the locking function under large loads. In general, the mechanical stop 504 prevents a lower portion of the integral locking mechanism—that portion that extends substantially normal to the interior wall of the housing—from moving past a normal or ninety degree orientation where further displacement of the shaft will not provide additional frictional force against the interior wall. It will be appreciated that the mechanical stop 504 may be usefully incorporated into any of the embodiments described above. For example, in the embodiment of FIG. 3, the mechanical stop 504 may be positioned to prevent the second plurality of members from hinging beyond a predetermined angle relative to the interior wall of the housing, such as beyond ninety degrees where increased force would no longer yield increased frictional loading against the interior wall.

Operation of a surgical puncture access device is now described in greater detail with reference to a puncture operation.

Figure 6:
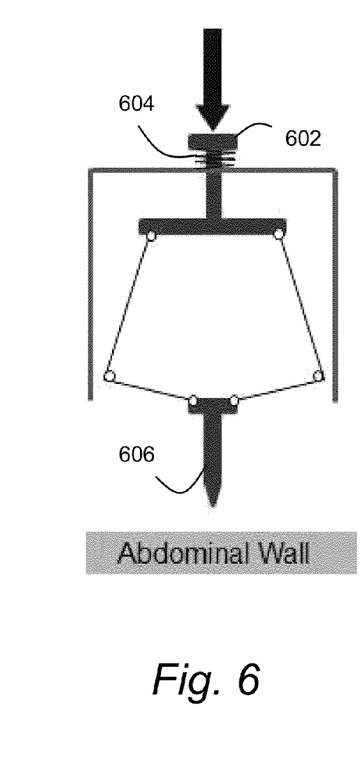
FIG. 6 depicts spring loading of a device.

FIG. 6 depicts spring loading of a device. In an initial step, a plunger 602 or other mechanical control is depressed to create a bias force against a spring 604. In this state, a functional tip 606 is deployed, but there is no force independent of the plunger 602 maintaining the functional tip 606 in this position.

Figure 7:
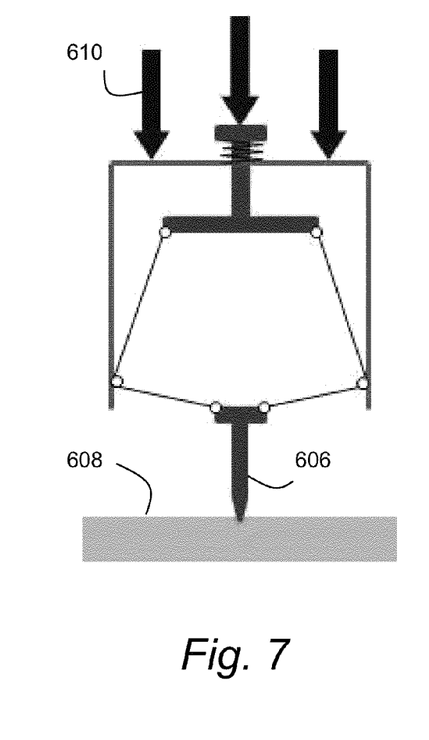
FIG. 7 depicts locking of a spring-loaded device.

FIG. 7 depicts locking of a spring-loaded device. In this step, the device is pressed against a target surface such as an abdominal wall 608 of a surgical patient. Thus the force applied to the functional tip 606 may be created by applying an axial force to the housing of the device (as indicated by arrows 610) while the cutting edge or other functional tip 606 engages a tissue layer of a patient. While an abdominal wall 608 is depicted, it will be understood that this tissue layer may also or instead include skin, muscle, peritoneum, or any other superficial layer of tissue, depending on whether and to what extent skin and other layers are surgically exposed prior to use of the device. The axial force may be obtained by a user gripping the device in any suitable manner and applying an axial load toward the target surface. It will be noted that at the moment of engagement with the target surface, two complementary forces—a first force applied to the plunger and a second force applied to the functional tip 606—are used to secure the instrument in the deployed position. These two complementary forces create the outward or normal force on the interior wall of the housing that frictionally engages the locking mechanism. However, once so engaged, the force on the functional tip 606 can sustain the locking effect and the force applied to the plunger may be removed, thus permitting free manipulation of the housing by a user, provided the functional tip 606 remains forcibly engaged with the target surface.

Figure 8:
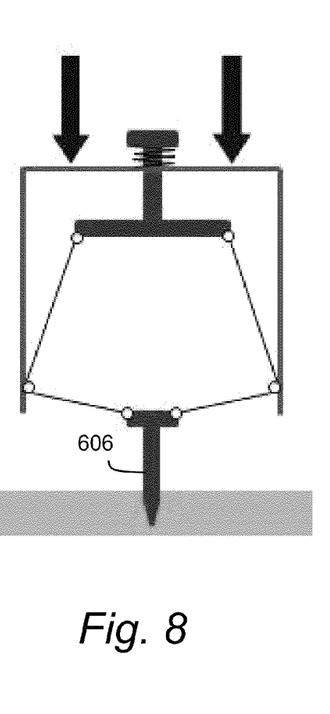
FIG. 8 depicts initiation of a puncture with a spring-loaded device.

FIG. 8 depicts initiation of a puncture with a spring-loaded device. In this step, the housing may be manually driven into the target surface so that the cutting edge of the instrument can puncture the surface. The force manually applied to the housing is directly translated to the functional tip 606 to obtain this cutting action.

Figure 9:
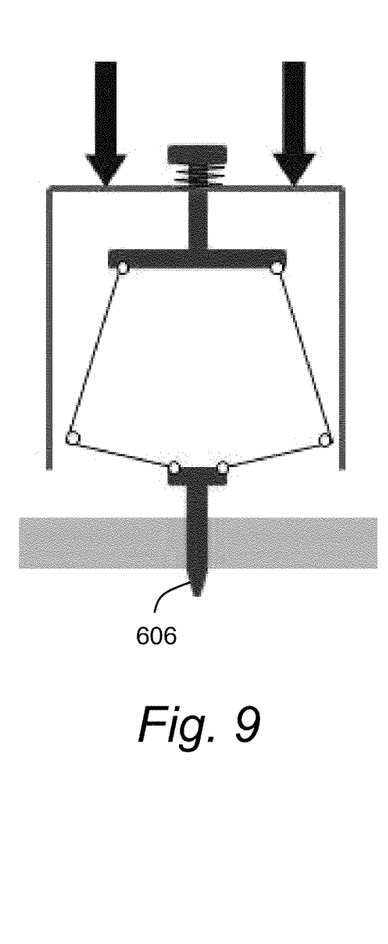
FIG. 9 depicts completion of a puncture with a spring-loaded device.

FIG. 9 depicts completion of a puncture with a spring-loaded device. In this step, the functional tip 606 has been driven through the surface. When the cutting edge of the functional tip 606 punctures the target surface (e.g., peritoneum of a patient), the force against the functional tip 606 is removed, and so is the resulting normal force against the housing. Without this normal force to secure frictional engagement with the housing, the locking mechanism can separate from the interior wall of the housing. This is illustrated as a small gap between the locking mechanism and the interior wall of the housing, however, physical separation of the surfaces is not required. The desired reduction in frictional engagement may be achieved while the two surfaces remain in contact, albeit under a reduced normal force.

Figure 10:
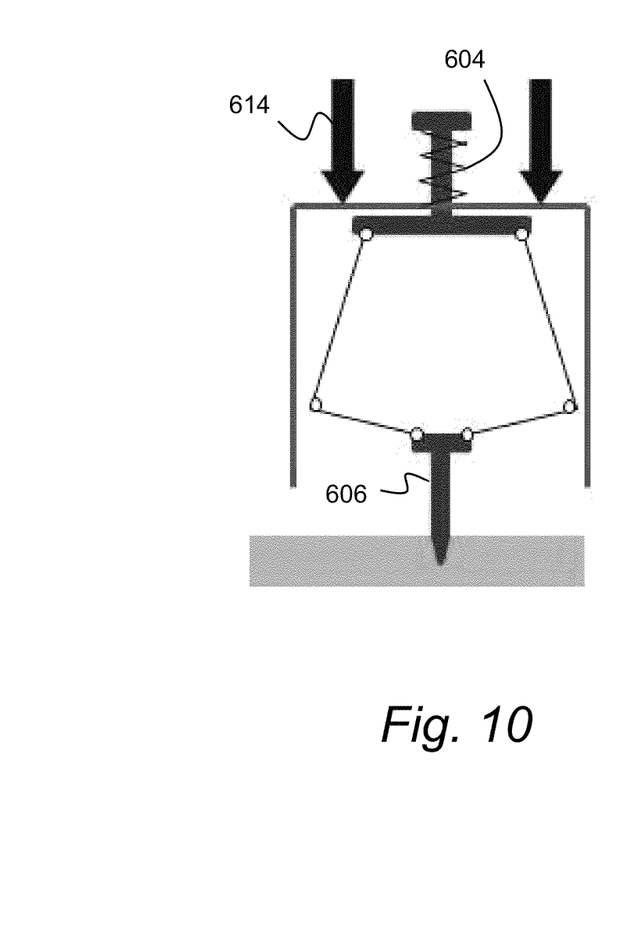
FIG. 10 depicts retraction of a blade of spring-loaded device.

FIG. 10 depicts retraction of a blade of spring-loaded device. When the frictional engagement of the locking mechanism to the interior wall is reduced or removed, the spring 604 can operate to retract the functional tip 606 in a direction opposite to the driving force 614 on the housing, thereby retracting the functional tip 606 at the moment of puncture and mitigating the over-puncture event.

Figure 11:
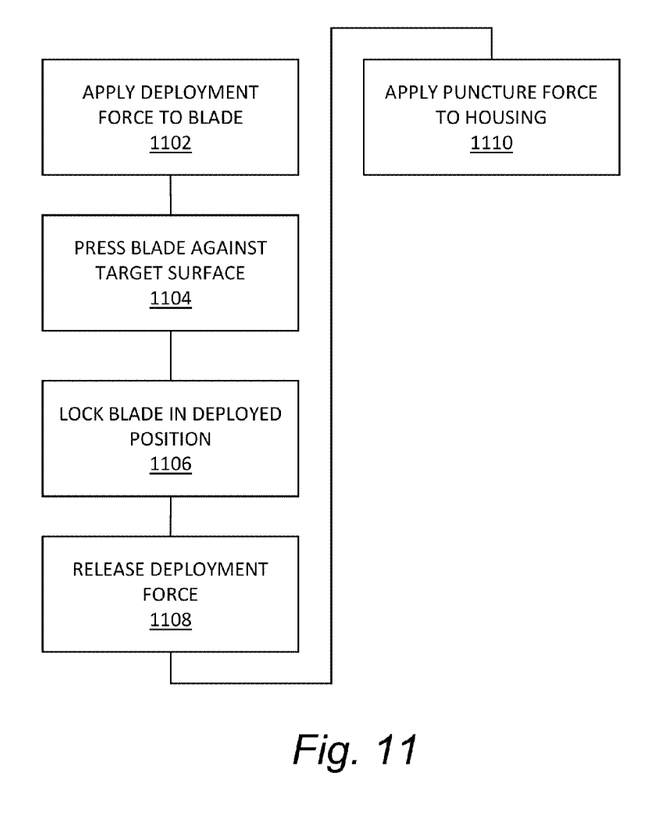
FIG. 11 is a flow chart of a method for surgical puncture access.

FIG. 11 is a flow chart of a method for surgical puncture access. The method 1100 may be performed using any of the devices described above.

As shown in step 1102, the method 1100 may begin with applying a deployment force to spring load a blade in a deployed position exposed outside a housing with a bias to return to a retracted position within the housing. This may, for example, include depressing a plunger or other control mechanism on the housing of the device. The bias may be achieved for example with a coil spring or any other suitable spring or elastic mechanism, or any combination of the foregoing that can provide sufficient biasing force to retract the blade or other functional tip as contemplated herein.

As shown in step 1104, the method 1100 may include pressing the blade against a target surface while in the deployed position, thereby creating a force against the blade.

As shown in step 1106, the method 1100 may include locking the blade in the deployed position by directing the force against the blade normally against an interior wall of the housing to establish a friction fit proportional to the force. This locking step is performed mechanically by the components of the device in response to the user-controlled steps of spring loading as in step 1102 and engagement with a target surface as in step 1104.

As shown in step 1108, the method may include releasing the deployment force on the plunger or other control mechanism. With the locking obtained in step 1106 and sustained force of the blade against a target surface, the blade can remain locked in the deployed position notwithstanding a driving force (e.g., by the hand of a user) of the housing and blade into the target surface. Thus, the hands of a user are free to manipulate the deployed blade to obtain a puncture of the target surface in any desire manner.

As shown in step 1110, a puncture force may be applied to the housing. This puncture force, which may be any suitable surgical puncture action or technique that maintains a force of the blade against the target surface, may drive the blade through the target surface. As a result, the force against the blade is released and the bias in the spring or other biasing mechanism can withdraw the blade into the retracted position. A similar effect may be achieved by simply removing the blade from the target surface, which would also remove the force against the blade, release the locking mechanism, and cause the spring to retract the blade into the housing. In order to resume the procedure from this state, the blade can once again be deployed with a deployment force as described in step 1102 and the method 1100 may be repeated.

It will be appreciated that the methods and systems described above are set forth by way of example and not of limitation. Numerous variations, additions, omissions, and other modifications will be apparent to one of ordinary skill in the art. While particular embodiments of the present invention have been shown and described, it will be apparent to those skilled in the art that various changes and modifications in form and details may be made without departing from the spirit and scope of the invention as defined by the following claims. The claims that follow are intended to include all such variations and modifications that might fall within their scope, and should be interpreted in the broadest sense allowable by law.

What is claimed is:

1. A device comprising:
   a housing having an interior with an axis;
   an instrument slidably retained within the housing and movable along the axis between a first position wherein a functional tip of the instrument extends outside the housing and a second position wherein the functional tip is disposed within the housing;
   a mechanical control to move the instrument from the second position to the first position, wherein the mechanical control includes a plunger;
   a locking mechanism configured to secure the instrument against movement toward the second position with a locking force when the instrument is in the first position and a force is applied to the functional tip of the instrument along the axis and toward the housing, wherein the locking force increases with the force applied to the functional tip, the locking mechanism further configured to release the instrument to move toward the second position when the force is removed; and
   a biasing mechanism that biases the instrument toward the second position, wherein the biasing mechanism includes a coil spring coupled to the plunger and the housing.

2. The device of claim 1 wherein the housing includes a trocar shaped and sized for use in a laparoscopic procedure.

3. The device of claim 1 wherein the instrument includes a cutting instrument.

4. The device of claim 1 wherein the functional tip includes a cutting edge.

5. The device of claim 4 wherein the force is applied to the functional tip by applying an axial force to the housing while the cutting edge engages a tissue layer of a surgical patient.

6. The device of claim 4 wherein the force is removed when the cutting edge punctures the tissue layer.

7. The device of claim 1 wherein the plunger is operable at a first end of the housing distal from a second end of the housing where the functional tip of the instrument extends outside the housing.

8. A device comprising:
   a housing having an axis;
   an instrument slidably retained within the housing and movable along the axis between a first position wherein a functional tip of the instrument extends outside the housing and a second position wherein the functional tip rests within the housing;
   a plunger coupled to the instrument to permit movement of the instrument between the first position and the second position;
   a biasing mechanism that biases the instrument toward the second position, wherein the biasing mechanism includes a coil spring coupled to the plunger and the housing; and
   a locking mechanism that secures the instrument against moving from the first position to the second position by frictionally engaging an interior wall of the housing with a force that increases a locking effect of frictional engagement as a load applied to the functional tip increases in a direction from the first position to the second position along the axis of the housing.

9. The device of claim 8 wherein the housing includes a trocar shaped and sized for use in a laparoscopic procedure.

10. The device of claim 8 wherein the instrument includes a cutting instrument.

11. The device of claim 8 wherein the functional tip includes a cutting edge.

12. The device of claim 8 wherein the plunger is operable at a first end of the housing distal from a second end of the housing where the functional tip of the instrument extends outside the housing.

* * * * *